United States Patent
Cornish et al.

(10) Patent No.: US 7,414,019 B2
(45) Date of Patent: Aug. 19, 2008

(54) FGF-8 METHODS OF USE

(75) Inventors: Jillian Cornish, Auckland (NZ); Ian Reginald Reid, Auckland (NZ); Jianming Lin, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 304 days.

(21) Appl. No.: 10/678,712

(22) Filed: Oct. 3, 2003

(65) Prior Publication Data

US 2004/0266680 A1    Dec. 30, 2004

Related U.S. Application Data

(60) Provisional application No. 60/416,377, filed on Oct. 4, 2002.

(51) Int. Cl.
*A61K 38/00* (2006.01)
*A61K 38/18* (2006.01)

(52) U.S. Cl. ............................................. 514/2; 514/12

(58) Field of Classification Search ........................ None
See application file for complete search history.

(56) References Cited

U.S. PATENT DOCUMENTS

2003/0022170 A1 * 1/2003 Khodadoust .................. 435/6

FOREIGN PATENT DOCUMENTS

WO    WO 01/00662    *    1/2001

OTHER PUBLICATIONS

Valta et al. Endorcrinol. 2006; 147: 2171-82.*
Yao et al. Brain research. 1999; 818: 140-146.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Blunt et al. "Overlapping Expression and Redundant Activation of Mesenchymal Fibroblast Growth Factor (FCF) Receptors by Alternatively Spliced FGF-8 Ligands" *J. of Biol. Chem.* 272(6):3733-3738 (1997).
Cornish et al. "Adrenomedullin is a potent stimulator of osteoblastic activity in vitro and in vivo" *Am. J. Physiol.* 273:E1113-E1120 (1997).
Cornish et al. "Systemic administration of a novel octapeptide, amylin-(1—8), increases bone volume in male mice" *Am. J. Physiol.* 279:E730-E735 (2000).
Cornish et al. "Trifluoroacetate, a contaminant in purified proteins, inhibits proliferation of osteoblasts and chondrocytes" *Am. J. of Physiol.* 277:E779-E783 (1999).
Genbank GI No. 1184864, Jan. 18, 1996.
Genbank GI No. 18461160, Jan. 30, 2002.
Genbank GI No. 619919, Dec. 15, 1994.
MacArthur et al. "*Fgf-8*, Activated by Proviral Insertion, Cooperates with the *Wnt-1* Transgene in Murine Mammary Tumorignesis" *J. of Virology* 69)4):2501-2507 (1995).
Moftah et al. "Ectodermal FGFs Induce Perinodular Inhibition of Limb Chondrogenesis in Vitro and in Vivo via FGF Receptor 2" *Dev. Biol.* 249:270-282 (2002).
Motulsky et al. "The Kinetics of Competitive Radioligand Binding Predicted by the Law of Mass Action" *Mol. Pharmacol.* 25:1-9 (1984).

* cited by examiner

*Primary Examiner*—Elizabeth C. Kemmerer
*Assistant Examiner*—Christina Borgeest
(74) *Attorney, Agent, or Firm*—Occhiuti Rohlicek & Tsao LLP

(57) ABSTRACT

This invention features a method for treating a bone condition in a patient, e.g., a mammal, a human, a horse, a dog, or a cat. The method includes administering an effective amount of FGF-8, FGF-8 analog, or a FGF-8 agonist to the patient.

12 Claims, 3 Drawing Sheets

The growth rate was assessed by [³H]-thymidine incorporation

The growth rate was assessed by [³H]-thymidine incorporation

FGF-8 METHODS OF USE

CROSS-REFERENCE TO RELATED APPLICATIONS

This application claims the benefit of U.S. provisional application Ser. No. 60/416,377, filed Oct. 4, 2002.

BACKGROUND

The fibroblast growth factors (FGFs) are a group of structurally related peptides with at least 23 family members identified to date. FGFs specify the differentiation, patterning, and proliferation of a variety of tissues. FGF-8 is thought to play a role in limb bud patterning and development as well as midbrain development. In the early stages of embryogenesis, FGF-8 is expressed in developing brains, limbs, heart, lung, skeleton, teeth, and the renal system. Application of FGF-8 to embryos induces the formation of brains and ectopic limbs, consistent with the role of FGF-8 in developmental processes. FGF-8-null mice have an embryonic lethal phenotype. In adult tissues, low levels of expression have been detected in heart, brain, lung, kidney, testis, prostate, and ovary.

The FGF-8 gene has 6 exons that potentially encode 8 isoforms. Seven isoforms of FGF-8 have been detected, with differences mapping to the N-terminal region (Blunt, A. G., et al. (1997) *J. Biol. Chem.* 272:3733-3738). The significance of these isoforms is unclear. FGF-8b displays the most potent mitogenic activity in vitro as compared to FGF-8a, -8c, -8d, -8e, -8f, and -8g isoforms (Blunt, A. G., et al., supra). FGF-8a does not stimulate mitogenesis through the known FGF receptors, unlike the other FGF-8 isoforms (Blunt, A. G., et al., supra). FGF-8 has been shown to modulate chondrogenesis (Moftah M, et al. (2002) *Dev. Biol. September* 15; 249 (2):270) but the involvement of FGF-8 in bone formation is unknown.

FGF-8 is highly homologous to FGF-13, FGF-17, and FGF-18, containing more than 50% amino acid identity with each.

SUMMARY

The present invention is based, in part, on the discovery that FGF-8 can stimulate proliferation of osteoblasts, which are known to play a role in mediating or modulating bone growth.

In one aspect, this invention features a method for treating a bone condition in a patient, e.g., a mammal, a human, a horse, a dog, or a cat. The method includes administering an effective amount of FGF-8, FGF-8 analog, or a FGF-8 agonist to the patient.

The patient can be at risk for, or suffering from a disease associated with excessive resorption or breakdown of bone tissue. Examples of such diseases include, but are not limited to, osteoporosis, osteopenia, bone defects, and osteogenesis imperfecta. The patient can also be suffering from bone loss as a result of immobility, bone fractures, malignancy, primary hyperparathyroidism, endocrine disorders, autoimmune arthritis, or addictive drug use. The patient can also be undergoing a treatment (e.g., corticosteroid treatment, bone marrow transplantation, or oophorectomy) known to result in bone loss. The term "bone condition" refers to any disease or symptom wherein osteoblast or osteoclast activity (or levels) is involved, and includes any of the diseases or situations described above.

As used herein, "FGF-8a" is an isolated polypeptide of 204 amino acids in length. It includes mouse FGF-8a, rat FGF-8, and human FGF-8a, the sequences of which are shown below.

Mouse FGF-8a:

MGSPRSALSCLLLHLLVLCLQAQHVREQSLVTDQLS (SEQ ID NO: 1)
RRLIRTYQLYSRTSGKHVQVLANKRINAMAEDGDPF
AKLIVETDTFGSRVRVRGAETGLYICMNKKGKLIAK
SNGKGKDCVFTEIVLENNYTALQNAKYEGWYMAFTR
KGRPRKGSKTRQHQREVHFMKRLPRGHHTTEQSLRF
EFLNYPPFTRSLRGSQRTWAPEPR

Rat FGF-8:

MGSPRSALSCLLLHLLVLCLQAQHVREQSLVTDQLS (SEQ ID NO: 2)
RRLIRTYQLYSRTSGKHVQVLANKRINAMAEDGDPF
AKLIVETDTFGSRVRVRGAETGLYICMNKKGKLIAK
SNGKGKDCVFTEIVLENNYTALQNAKYEGWYMAFTR
KGRPRKGSKTRQHQREVHFMKRLPRGHHTTEQSLRF
EFLNYPPFTRSLRGSQRTWAPEPRL

Human FGF-8:

MGSPRSALSCLLLHLLVLCLQAQHVREQSLVTDQLS (SEQ ID NO: 3)
RRLIRTYQLYSRTSGKHVQVLANKRINAMAEDGDPF
AKLIVETDTFGSRVRVRGAETGLYICMNKKGKLIAK
SNGKGKDCVFTEIVLENNYTALQNAKYEGWYMAFTR
KGRPRKGSKTRQHQREVHFMKRLPRGHHTTEQSLRF
EFLNYPPFTRSLRGSQRTWAPEPR.

The mouse FGF-8a DNA sequence is as follows:

CGCACCTTCGGCTTGTCCCCCGCGGCCTCCAGTGGGACGGCGTGACCCC
GCTCGGGCTCTCAGTGCTCCCGGGGCCGCGCGCCATGGGCAGCCCCCGCT
CCGCGCTGAGCTGCCTGCTGTTGCACTTGCTGGTTCTCTGCCTCCAAGCC
CAGCATGTGAGGGAGCAGAGCCTGGTGACGGATCAGCTCAGCCGCCGCCT
CATCCGGACCTACCAGCTCTACAGCCGCACCAGCGGGAAGCACGTGCAGG
TCCTGGCCAACAAGCGCATCAACGCCATGGCAGAAGACGGAGACCCCTTC
GCGAAGCTCATTGTGGAGACCGATACTTTTGGAAGCAGAGTCCGAGTTCG
CGGCGCAGAGACAGGTCTCTACATCTGCATGAACAAGAAGGGGAAGCTAA
TTGCCAAGAGCAACGGCAAAGGCAAGGACTGCGTATTCACAGAGATCGTG
CTGGAGAACAACTACACGGCGCTGCAGAACGCCAAGTACGAGGGCTGGTA
CATGGCCTTTACCCGCAAGGGCCGGCCCCGCAAGGGCTCCAAGACGCGCC
AGCATCAGCGCGAGGTGCACTTCATGAAGCGCCTGCCGCGGGGCCACCAC
ACCACCGAGCAGAGCCTGCGCTTCGAGTTCCTCAACTACCCGCCCTTCAC
GCGCAGCCTGCGCGGCAGCCAGAGGACTTGGGCCCCGGAGCCCCGATAGG

-continued

CGCTCGCCCAGCTCCTCCCCACCCAGCCGGCCGAGGAATCCAGCGGGAGC

TCG (SEQ ID NO: 4; see also Genbank ® GI No. 619919)

The rat FGF-8 DNA sequence is as follows:

ATGGGCAGCCCCGCTCCGCGCTGAGCTGCCTGCTGTTGCACTTGCTGGT

TCTCTGCCTCCAAGCCCAGCATGTGAGGGAGCAGAGCCTGGTGACGGATC

AGCTCAGCCGCCGCCTCATCCGGACCTACCAGCTCTACAGCCGCACCAGC

GGGAAGCACGTGCAGGTCCTGGCCAACAAGCGCATCAACGCCATGGCAGA

AGACGGAGACCCCTTCGCAAAGCTCATTGTGGAGACCGATACTTTTGGAA

GCAGAGTCCGAGTCCGCGGAGCAGAGACCGGTCTGTACATCTGCATGAAC

AAGAAGGGGAAGCTAATCGCCAAGAGCAACGGCAAAGGCAAGGACTGCGT

GTTCACGGAGATCGTGCTGGAGAACAACTACACGGCGCTGCAGAACGCCA

AGTACGAGGGCTGGTACATGGCCTTTACCCGCAAGGGCCGGCCCCGCAAG

GGTTCCAAGACGCGCCAGCACCAGCGCGAGGTGCACTTCATGAAGCGCCT

GCCGCGGGGCCACCACACCACAGAGCAGAGCCTCCGCTTCGAGTTCCTCA

ACTACCCGCCCTTCACGCGCAGCCTGCGCGGCAGCCAGAGGACTTGGGCC

CCGGAGCCCCGATAG (SEQ ID NO: 5; see also Genbank ® GI No. 18461160)

The sequence of human FGF-8a is as follows:

ATGGGCAGCCCCGCTCCGCGCTGAGCTGCCTGCTGTTGCACTTGCTGGT

CCTCTGCCTCCAAGCCCAGCATGTGAGGGAGCAGAGCCTGGTGACGGATC

AGCTCAGCCGCCGCCTCATCCGGACCTACCAACTCTACAGCCGCACCAGC

GGGAAGCACGTGCAGGTCCTGGCCAACAAGCGCATCAACGCCATGGCAGA

GGACGGCGACCCCTTCGCAAAGCTCATCGTGGAGACGGACACCTTTGGAA

GCAGAGTCCGAGTCCGAGGAGCCGAGACGGGCCTCTACATCTGCATGAAC

AAGAAGGGGAAGCTGATCGCCAAGAGCAACGGCAAAGGCAAGGACTGCGT

CTTCACGGAGATTGTGCTGGAGAACAACTACACAGCGCTGCAGAATGCCA

AGTACGAGGGCTGGTACATGGCCTTCACCCGCAAGGGCCGGCCCCGCAAG

GGCTCCAAGACGCGGCAGCACCAGCGTGAGGTCCACTTCATGAAGCGGCT

GCCCCGGGGCCACCACACCACCGAGCAGAGCCTGCGCTTCGAGTTCCTCA

ACTACCCGCCCTTCACGCGCAGCCTGCGCGGCAGCCAGAGGACTTGGGCC

CCGGAGCCCCGATAG (SEQ ID NO: 6; see also Genbank ® GI No. 1184864)

Analogs of FGF-8 include functional equivalents of FGF-8 (e.g., functional equivalents of mouse FGF-8, human FGF-8, or rat FGF-8). In terms of FGF-8 itself, functional equivalents include all proteins which are immunologically cross-reactive with and have substantially the same function as FGF-8 (e.g., any of SEQ ID NOs: 1-3). That equivalent may, for example, be a fragment of FGF-8 containing a subsequence of amino acids (e.g., a truncation) and including a FGF-8 active site or sites, a substitution, addition or deletion mutant of FGF-8, or a fusion of FGF-8 or a fragment or a mutant with other amino acids.

A "FGF-8 agonist" is a compound which (1) has a high affinity (e.g., a Ki of $10^{-7}$-$10^{-9}$ M, a Ki of $10^{-8}$-$10^{-9}$ M) for a FGF-8-binding receptor (as defined by the receptor binding assay described in Motulsky, H. J and Mahan, L. C. (1984). *Mol. Pharmacol.* 25: 1; and (2) promotes the proliferation of bone cells, e.g., osteoblasts.

In one embodiment, the methods described herein include administering to a patient an effective amount of FGF-8 having the amino acid sequence of SEQ ID NO: 1, 2, or 3.

In another embodiment, the method includes administering to a patient an effective amount of a FGF-8 agonist having a fragment (e.g., any sequence between about 10 and 200, alternatively between about 10 and 100, alternatively between about 10 and 50, alternatively between about 10 and 25 amino acids in length, inclusive, of SEQ ID NO: 1, 2, or 3); or the entirety of the amino acid sequence of SEQ ID NO: 1, 2, or 3. For example, a FGF-8 agonist is a peptide being less than 87 amino acids in length, e.g., a peptide having less than 30 amino acids, or more than 10 (e.g., any integer between 10 and 90, inclusive) amino acids, and containing, in consecutive sequence, any part of SEQ ID NO: 1, 2, or 3.

In a further embodiment, the method includes administering to a patient an effective amount of a FGF-8 agonist containing an amino acid sequence that is at least 60% (e.g., 70%, 80%, 90%, 95%, or 98%) identical to SEQ ID NO: 1, 2, or 3. The "percent identity" of two amino acid sequences can be determined using the algorithm of Karlin and Altschul (1990, *Proc. Natl. Acad. Sci. USA* 87: 2264-2268), modified as in Karlin and Altschul (1993, *Proc. Natl. Acad. Sci. USA* 90: 5873-5877). Such an algorithm is incorporated into the NBLAST and XBLAST programs (version 2.0) of Altschul et al. (1990) *J. Mol. Biol.* 215: 403-10. BLAST protein searches can be performed with the XBLAST program, score=50, wordlength=3 to obtain amino acid sequences homologous to the peptide molecules described herein. Where gaps exist between two sequences, Gapped BLAST can be utilized as described in Altschul et al. (1997) *Nucleic Acids Res.* 25(17): 3389-3402. When utilizing BLAST and Gapped BLAST programs, the default parameters of the respective programs (e.g., XBLAST and NBLAST) can be used.

In still another embodiment, the method includes administering to a patient an effective amount of a FGF-8 agonist containing SEQ ID NO: 1, 2, or 3 with up to 14 (e.g., any integer between 1 and 14, inclusive) conservative amino acid substitutions. A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid analogs (e.g., phosphorylated amino acids) are also contemplated in the present invention.

In another aspect, this invention features a method for increasing or maintaining bone density. The method includes administering to a subject (e.g., a mammal, a human, a horse, a dog, or a cat) in need thereof an effective amount of FGF-8, FGF-8 analog, or a FGF-8 agonist as described herein. As used herein, the subject may have a substantially normal bone density or the subject may be at risk of bone deterioration. Examples of these subjects include postmenopausal women, usually at age 50 and over, and men over 60 years of age.

In another aspect, the invention features a method for treating or preventing an FGF-8-mediated bone disease. The method includes administering to a subject (e.g., a mammal, a human, a horse, a dog, or a cat) in need thereof an effective amount of FGF-8, FGF-8 analog, or a FGF-8 agonist as described herein.

In a further aspect, this invention features a method for stimulating osteoblast growth or modulating osteoblast apoptosis. The method includes administering to a subject in need thereof an effective amount of FGF-8, FGF-8 analog, or a FGF-8 agonist. The term "osteoblast" refers to bone-forming cells.

This invention also features an article of manufacture that includes a vessel containing FGF-8, a FGF-8 analog, a FGF-8 agonist, or a nucleic acid encoding FGF-8, a FGF-8 analog, or a FGF-8 agonist; and instructions for use of FGF-8, FGF-8 analog, or a FGF-8 agonist for treatment of a bone condition by administering an effective amount of FGF-8, FGF-8 analog, or a FGF-8 agonist to a patient.

Also within the scope of this invention is an article of manufacture. The article includes packaging material; and contained within the packaging material, FGF-8, FGF-8 analog, or a FGF-8 agonist. The packaging material comprises a label that indicates that FGF-8, FGF-8 analog, or a FGF-8 agonist can be used for treating a bone condition (e.g., osteoporosis, osteopenia, bone defects, or osteogenesis imperfecta) in a patient. In other aspects, the label includes dosage information.

Other features, objects, and advantages of the invention will be apparent from the description and drawings, and from the claims.

DETAILED DESCRIPTION

Figure 1:
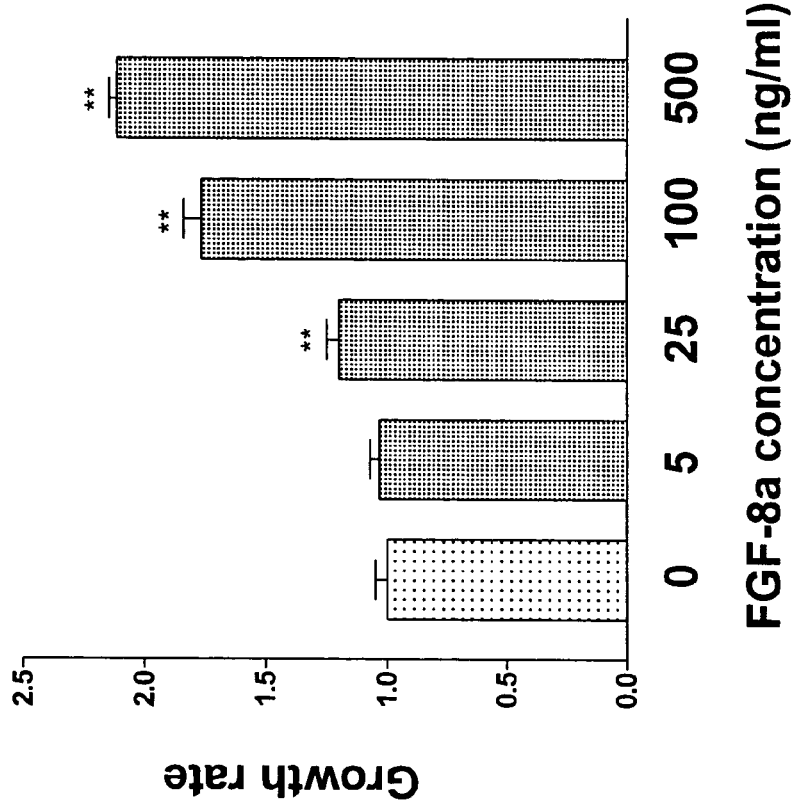
FIG. 1 depicts the effect of various concentrations of FGF-8a or vehicle on thymidine incorporation by rat osteoblasts. ** represents $p<0.01$, and * represents $p<0.05$.

This invention relates to use of FGF-8, a FGF-8 analog, or a FGF-8 agonist for stimulating osteoblast growth or modulating osteoblast apoptosis. FGF-8, as well as a FGF-8 analog or FGF-8 agonist, also can be prepared by a synthetic method. More specifically, synthesis of peptides (e.g., peptides derived from FGF-8) is well established in the art. See, e.g., Stewart, et al. (1984) Solid Phase Peptide Synthesis ($2^{nd}$ Ed.); and Chan (2000) "Fmoc Solid Phase Peptide Synthesis, A Practical Approach," Oxford University Press. The peptides may be synthesized using an automated peptide synthesizer (e.g., a Pioneer™ Peptide Synthesizer, Applied Biosystems, Foster City, Calif.). For example, a peptide is prepared on methylbenzyhydrylamine resin followed by hydrogen fluoride deprotection and cleavage from the resin. The synthesized peptide can be further purified by a method such as affinity column chromatography or high pressure liquid chromatography. Standard physicochemical characterization techniques are known in the art, including NMR ($^{13}$C, $^{1}$H, $^{19}$F, or $^{31}$P) and IR, which can provide confirmatory evidence of the identity and purity of the synthetic products. Amino acid analysis can also be used to confirm the amino acid composition of the peptide. Laser desorption mass spectroscopy can be used to identify the molecular weight of synthetic products.

One aspect of this invention is a method for treating a bone condition with an effective amount of a FGF-8, FGF-8 analog, or a FGF-8 agonist. Another aspect of this invention is a method for increasing or maintaining bone density with a FGF-8, FGF-8 analog, or a FGF-8 agonist. The term "treating" is defined as the application or administration of a composition including a FGF-8, FGF-8 analog, or a FGF-8 agonist to a patient, who has, or is determined to have, a bone condition, a symptom of a bone condition, a disease or disorder secondary to a bone condition, or a predisposition toward a bone condition, with the purpose to cure, alleviate, relieve, remedy, or ameliorate the bone condition, the symptom of the bone condition, the disease or disorder secondary to the bone condition, or the predisposition toward the bone condition.

"An effective amount" refers to an amount of FGF-8, FGF-8 analog, or a FGF-8 agonist that confers a therapeutic effect on the treated subject. The therapeutic effect may be objective (i.e., measurable by some test or marker) or subjective (i.e., subject gives an indication of or feels an effect). An effective amount of FGF-8, FGF-8 analog, or a FGF-8 agonist described above may range from about 1 µg/Kg body weight to about 1000 µg/Kg body weight. Effective doses will also vary depending on the route of administration, as well as the possibility of co-usage with other agents for stimulating osteoblast growth or modulating osteoblast apoptosis, such as a bone anti-resorptive agent (e.g., calcitonin or bisphosphonate) or a bone anabolic agent (e.g., parathyroid hormone, parathyroid hormone related protein, cytokines, or growth hormone).

As used herein, FGF-8, FGF-8 analog, and FGF-8 agonists are defined to include pharmaceutically acceptable derivatives (e.g., salts).

The methods delineated herein can also include the step of identifying that the subject is in need of treatment for the aforementioned disorders or condition. The identification can be in the judgment of a subject or a health care professional and can be a subjective (e.g., opinion) or objective (e.g., measurable by a test or diagnostic method).

The methods of treating delineated herein can include use or administration of a nucleic acid that encodes for FGF-8 (including all isoforms thereof), FGF-8 analog, or FGF-8 agonist, including those nucleic acids delineated as SEQ ID NOs. 4-6. See also, C. A. MacArthur et al., *J. of Virology*, (1995) 2501-2507. The nucleic acids described herein can be incorporated into gene constructs to be used as a part of a gene therapy protocol to deliver nucleic acids encoding FGF-8 (including all isoforms thereof), FGF-8 analog, or FGF-8 agonist. The invention features expression vectors for in vivo transfection and expression of a polypeptide described herein in particular cell types so as to reconstitute the function of, or alternatively, antagonize the function of a cell, relating to osteoblast or osteoclast function, and bone conditions. Expression constructs of such components may be administered in any biologically effective carrier, e.g. any formulation or composition capable of effectively delivering the component gene to cells, preferably adipose cells, in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. Retrovirus vectors and adeno-associated virus vectors can be used as a recombinant gene delivery system for the transfer of exogenous genes in vivo, particularly into humans.

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Pharmaceutically acceptable salts include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate, trifluoroacetate, and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and $N\text{-}(alkyl)_4^+$ salts. This invention also envisions the quaternization of any basic nitrogen-containing groups of the compounds disclosed herein. Water or oil-soluble or dispersible products may be obtained by such quaternization.

Also within the scope of this invention is a pharmaceutical composition that contains an effective amount of FGF-8, FGF-8 analog, or a FGF-8 agonist, and a pharmaceutically acceptable carrier. These compositions are suitable for use in the methods delineated herein.

The term "pharmaceutically acceptable carrier" refers to a carrier (adjuvant or vehicle) that may be administered to a patient, together with FGF-8, FGF-8 analog, or a FGF-8 agonist, and which does not destroy the pharmacological activity thereof and is nontoxic when administered in doses sufficient to deliver FGF-8, FGF-8 analog, or a FGF-8 agonist.

Pharmaceutically acceptable carriers that may be used in the pharmaceutical compositions described above include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents, which are commonly used in the formulation of pharmaceutically acceptable dosage forms such as emulsions and or suspensions.

FGF-8, a FGF-8 analog, or an FGF-8 agonist can be modified to increase stability or in vivo half life by linkage with a lipid, a carbohydrate, or other polymer. For example, FGF-8, a FGF-8 analog, or an FGF-8 agonist can be conjugated to a water soluble polymer, e.g., hydrophilic polyvinyl polymers. Such polymers include polyalkylene oxide homopolymers such as polyethylene glycol (PEG).

To practice the method for treating a bone condition or the method for increasing or maintaining bone density, FGF-8, FGF-8 analog, or a FGF-8 agonist can be administered to a patient or a subject. The FGF-8, FGF-8 analog, or the FGF-8 agonist can, for example, be administered in a pharmaceutically acceptable carrier such as physiological saline, in combination with other drugs, and/or together with appropriate excipients. It also can, for example, be administered by injection, intravenously, intraarterially, subdermally, intraperitoneally, intramuscularly, or subcutaneously; or orally, buccally, nasally, transmucosally, topically, in an ophthalmic preparation, by inhalation, by intracranial injection or infusion techniques. The methods herein contemplate administration of an effective amount of compound or compound composition to achieve the desired or stated effect. Lower or higher doses than those described above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

A pharmaceutical composition may be orally administered in any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

A sterile injectable composition (e.g., aqueous or oleaginous suspension) can be formulated according to techniques known in the art using suitable dispersing or wetting agents (such as, for example, Tween 80) and suspending agents.

Topical administration of a pharmaceutical composition is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-applied transdermal patches are also included in this invention.

A pharmaceutical composition may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

FGF-8 agonists can be tested for their abilities to stimulate osteoblast growth, modulate osteoblast apoptosis, or modulate osteoclast formation by examining their activities in the in vitro assays described herein. See the specific examples below. In vivo screening can also be performed by following procedures well known in the art. See, e.g., Cornish et al. (1997) *Am J Physiol* 273: E1113-E1120; and Cornish et al. (2000) *Am J Physiol* 279: E730-E735.

An effective amount of a compound described herein, or a composition described herein, can be administered to a subject (including a subject identified as in need of such treatment) to produce such effects as those described herein.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following examples. It should be understood that these examples are for illustrative purposes only and are not to be construed as limiting this invention in any manner.

EXAMPLE 1

Promoting Proliferation of Bone Cells

Osteoblast-Like Cell Culture. Osteoblasts were isolated from 20 day fetal rat calvariae as previously described (Cornish et al. (1999) *American Journal of Physiology—Endocrinology & Metabolism* 277: E779-E783). Briefly, calvariae were excised and the frontal and parietal bones, free of suture and periosteal tissue, were collected. The calvariae were sequentially digested using collagenase and the cells from digests 3 and 4 were collected, pooled and washed. Cells were grown to confluence and then subcultured into 24 well plates. Cells were growth arrested in minimum essential medium (MEM)/0.1% bovine serum albumin for 24 h. Fresh media and experimental compounds were added for a further 24 h. Cells were pulsed with tritiated-thymidine two hours before the end of the experimental incubation. The effect of FGF-8a on osteoblast proliferation was assessed by the measurement of [$^3$H]-thymidine incorporation into isolated primary osteoblasts and osteoblast-like cells.

Figure 2:
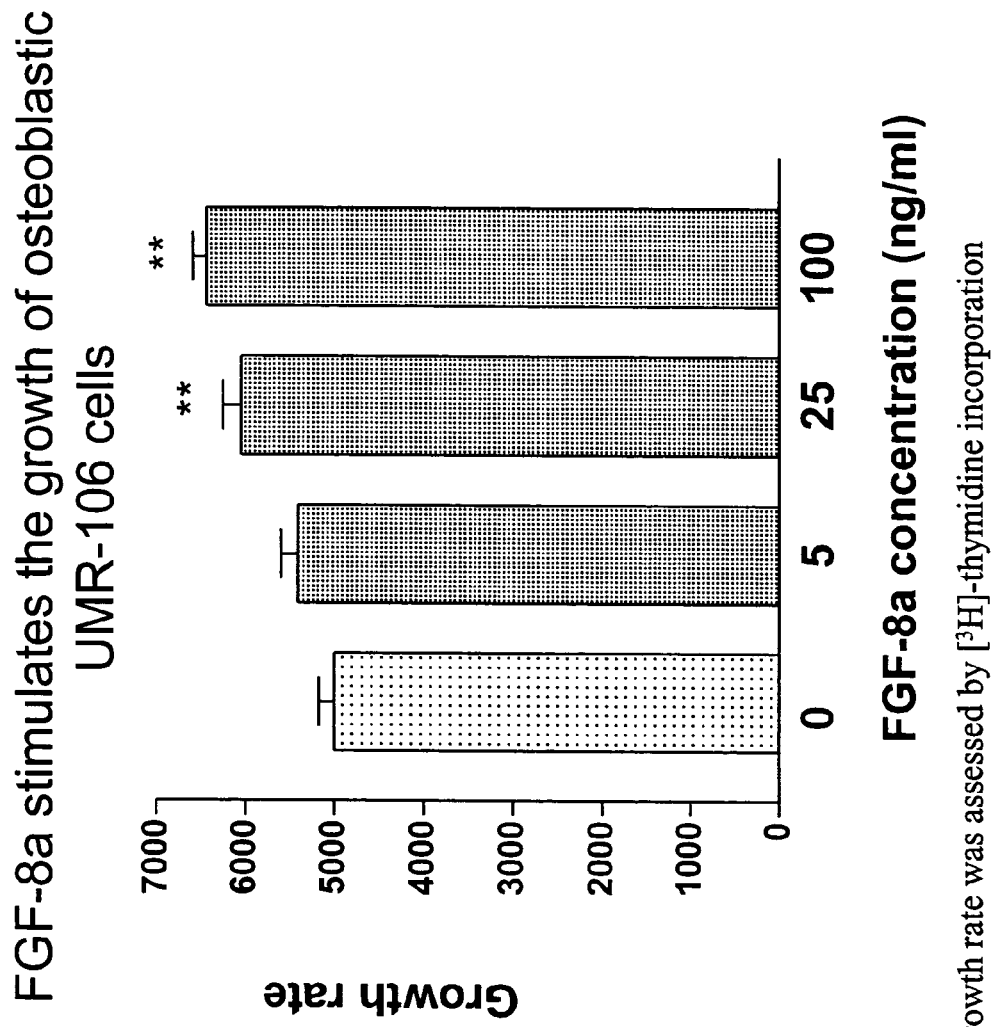
FIG. 2 depicts the effect of various concentrations of FGF-8a or vehicle on cell thymidine incorporation by osteoblastic UMR-106 cells. ** represents $p<0.01$.

As shown in FIGS. 1 and 2, FGF-8, in a dose-dependent manner, stimulated the proliferation ([$^3$H]-thymidine incorporation) of primary fetal rat osteoblasts and osteoblast-like cell lines at concentrations of >5 ng/ml.

EXAMPLE 2

Inhibiting Formation of Osteoclasts

Figure 3:
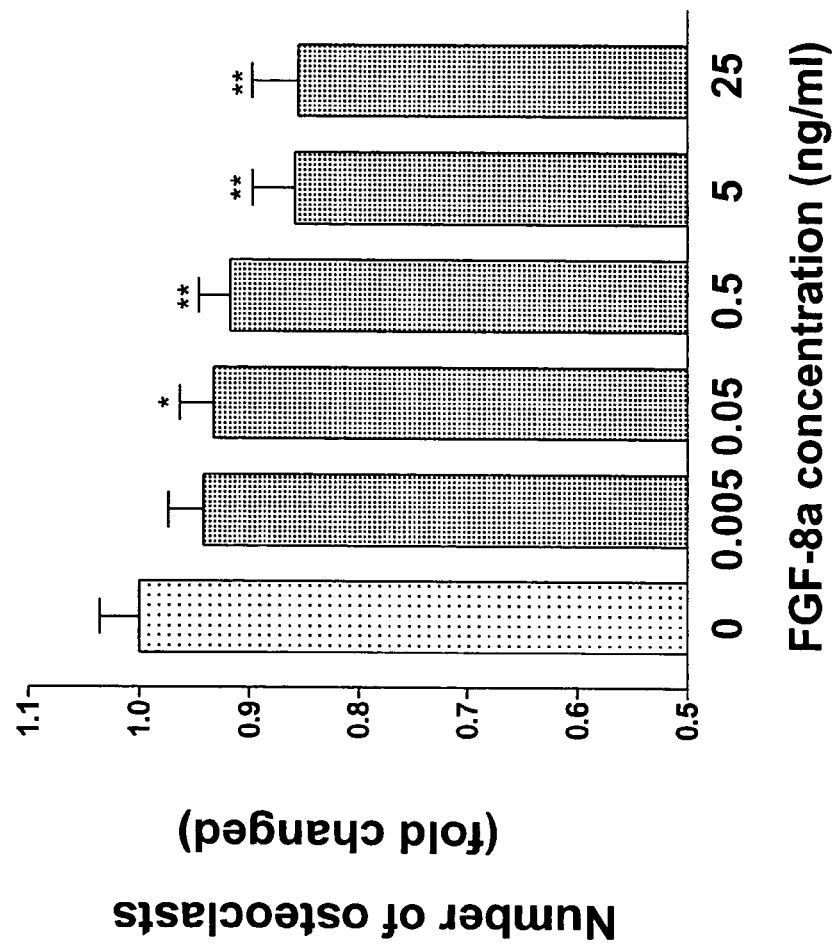
FIG. 3 depicts the effect of various concentrations of FGF-8a or vehicle on osteoclast formation from mouse bone marrow cultures. * represents $p<0.05$, and ** represents $p<0.01$.

Osteoclastogenesis assay. Bone marrow is obtained from the long bones of normal mice, aged 4-6 weeks were cultured. Non-adherent cells are removed and the cultures are grown in the presence of 1α,25-dihydroxyvitamin D3 throughout the experiment. The cultures were maintained for 7 days and the number of tartrate-resistant acid phosphatase-positive multinucleated cells was assessed. As shown in FIG. 3, FGF-8a inhibited the formation of osteoclasts in bone marrow cultures in a dose-dependent manner.

EXAMPLE 3

Expression of FGF-8 in Fetal Rat Brains and Cultured Osteoblasts

RT-PCR. RNA was collected. Briefly, RNA was extracted from primary fetal rat osteoblasts using a RNA extraction kit (Qiagen). RNA was quantitated by spectrophotometry and stored at −20° C. until further use. Semi-quantitative RT-PCR was performed using standard techniques to demonstrate the expression of the FGF-8 gene in the osteoblasts. Analysis of RT-PCR products by agarose gel electrophoresis showed that FGF-8 is expressed in fetal rat brain and cultured rat osteoblasts.

Other Embodiments

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a bone condition associated with excessive resorption or breakdown of bone tissue, comprising administering to a patient in need thereof FGF-8, or a FGF-8 agonist, wherein the FGF-8 comprises an amino acid sequence which is the amino acid sequence of SEQ ID NO:1, 2, or 3, wherein the FGF-8 agonist comprises an amino acid sequence at least 95% identical to the amino acid sequence of SEQ ID NO: 1, 2, or 3, and wherein FGF-8 or the FGF-8 agonist is administered in an amount effective to treat the bone condition in the patient.

2. The method of claim 1, wherein FGF-8 is administered.

3. The method of claim 1, wherein the FGF-8 agonist is administered, and wherein the FGF-8 agonist comprises an amino acid sequence that is at least 98% identical to SEQ ID NO: 1,2,or3.

4. The method of claim 1, wherein the FGF-8 agonist is administered, and wherein the FGF-8 agonist comprises SEQ ID NO: 1, 2, or 3 with up to 10 conservative amino acid substitutions.

5. A method for increasing or maintaining bone density, comprising administering to a subject in need thereof FGF-8, or a FGF-8 agonist, wherein the FGF-8 comprises an amino acid sequence which is the amino acid sequence of SEQ ID NO:1, 2, or 3, wherein the FGF-8 agonist comprises an amino acid sequence at least 95% identical to the amino acid sequence of SEQ ID NO: 1, 2, or 3, and wherein FGF-8 or the FGF-8 agonist is administered in an amount effective to increase or maintain bone density in the subject.

6. The method of claim 5, wherein FGF-8 is administered.

7. The method of claim 5, wherein the FGF-8 agonist is administered, and wherein the FGF-8 agonist comprises an amino acid sequence that is at least 98% identical to SEQ ID NO: 1, 2, or3.

8. The method of claim 5, wherein the FGF-8 agonist is administered, and wherein the FGF-8 agonist comprises SEQ ID NO: 1, 2, or 3 with up to 10 conservative amino acid substitutions.

9. A method for treating osteoporosis, osteopenia, bone defects, or osteogenesis imperfecta, comprising:

administration to a subject in need thereof FGF-8, or a FGF-8 agonist, wherein the FGF-8 comprises an amino acid sequence which is the amino acid sequence of SEQ ID NO:1, 2, or 3, wherein the FGF-8 agonist comprises an amino acid sequence at least 95% identical to the amino acid sequence of SEQ ID NO: 1, 2, or 3, wherein FGF-8 or the FGF-8 agonist is administered in an amount effective to treat the osteoporosis, osteopenia, bone defects, or osteogenesis imperfecta in the subject.

10. The method of claim 9, wherein FGF-8 is administered.

11. The method of claim 9, wherein the FGF-8 agonist is administered, and wherein the FGF-8 agonist comprises an amino acid sequence that is at least 98% identical to SEQ ID NO: 1, 2, or 3.

12. The method of claim 9, wherein the FGF-8 agonist is administered, and wherein the FGF-8 agonist comprises SEQ ID NO: 1, 2, or 3 with up to 10 conservative amino acid substitutions.

* * * * *

SEQUENCE LISTING

<160> NUMBER OF SEQ ID NOS: 6

<210> SEQ ID NO 1
<211> LENGTH: 204
<212> TYPE: PRT
<213> ORGANISM: Mus musculus

<400> SEQUENCE: 1

Met Gly Ser Pro Arg Ser Ala Leu Ser Cys Leu Leu Leu His Leu Leu
 1               5                  10                  15

Val Leu Cys Leu Gln Ala Gln His Val Arg Glu Gln Ser Leu Val Thr
            20                  25                  30

Asp Gln Leu Ser Arg Arg Leu Ile Arg Thr Tyr Gln Leu Tyr Ser Arg
        35                  40                  45

Thr Ser Gly Lys His Val Gln Val Leu Ala Asn Lys Arg Ile Asn Ala
    50                  55                  60

Met Ala Glu Asp Gly Asp Pro Phe Ala Lys Leu Ile Val Glu Thr Asp
65                  70                  75                  80

Thr Phe Gly Ser Arg Val Arg Val Arg Gly Ala Glu Thr Gly Leu Tyr
                85                  90                  95

Ile Cys Met Asn Lys Lys Gly Lys Leu Ile Ala Lys Ser Asn Gly Lys
            100                 105                 110

Gly Lys Asp Cys Val Phe Thr Glu Ile Val Leu Glu Asn Asn Tyr Thr
        115                 120                 125

Ala Leu Gln Asn Ala Lys Tyr Glu Gly Trp Tyr Met Ala Phe Thr Arg
    130                 135                 140

Lys Gly Arg Pro Arg Lys Gly Ser Lys Thr Arg Gln His Gln Arg Glu
145                 150                 155                 160

Val His Phe Met Lys Arg Leu Pro Arg Gly His His Thr Thr Glu Gln
                165                 170                 175

Ser Leu Arg Phe Glu Phe Leu Asn Tyr Pro Pro Phe Thr Arg Ser Leu
            180                 185                 190

Arg Gly Ser Gln Arg Thr Trp Ala Pro Glu Pro Arg
        195                 200

<210> SEQ ID NO 2
<211> LENGTH: 205
<212> TYPE: PRT
<213> ORGANISM: Rattus norvegicus

<400> SEQUENCE: 2

Met Gly Ser Pro Arg Ser Ala Leu Ser Cys Leu Leu Leu His Leu Leu
 1               5                  10                  15

Val Leu Cys Leu Gln Ala Gln His Val Arg Glu Gln Ser Leu Val Thr
            20                  25                  30

Asp Gln Leu Ser Arg Arg Leu Ile Arg Thr Tyr Gln Leu Tyr Ser Arg
        35                  40                  45

Thr Ser Gly Lys His Val Gln Val Leu Ala Asn Lys Arg Ile Asn Ala
    50                  55                  60

Met Ala Glu Asp Gly Asp Pro Phe Ala Lys Leu Ile Val Glu Thr Asp
65                  70                  75                  80

Thr Phe Gly Ser Arg Val Arg Val Arg Gly Ala Glu Thr Gly Leu Tyr
                85                  90                  95

Ile Cys Met Asn Lys Lys Gly Lys Leu Ile Ala Lys Ser Asn Gly Lys
            100                 105                 110

```
Gly Lys Asp Cys Val Phe Thr Glu Ile Val Leu Glu Asn Asn Tyr Thr
            115                 120                 125

Ala Leu Gln Asn Ala Lys Tyr Glu Gly Trp Tyr Met Ala Phe Thr Arg
        130                 135                 140

Lys Gly Arg Pro Arg Lys Gly Ser Lys Thr Arg Gln His Gln Arg Glu
145                 150                 155                 160

Val His Phe Met Lys Arg Leu Pro Arg Gly His His Thr Thr Glu Gln
                165                 170                 175

Ser Leu Arg Phe Glu Phe Leu Asn Tyr Pro Pro Phe Thr Arg Ser Leu
                180                 185                 190

Arg Gly Ser Gln Arg Thr Trp Ala Pro Glu Pro Arg Leu
            195                 200                 205

<210> SEQ ID NO 3
<211> LENGTH: 204
<212> TYPE: PRT
<213> ORGANISM: Homo sapiens

<400> SEQUENCE: 3

Met Gly Ser Pro Arg Ser Ala Leu Ser Cys Leu Leu His Leu Leu
1               5                   10                  15

Val Leu Cys Leu Gln Ala Gln His Val Arg Glu Gln Ser Leu Val Thr
            20                  25                  30

Asp Gln Leu Ser Arg Arg Leu Ile Arg Thr Tyr Gln Leu Tyr Ser Arg
        35                  40                  45

Thr Ser Gly Lys His Val Gln Val Leu Ala Asn Lys Arg Ile Asn Ala
    50                  55                  60

Met Ala Glu Asp Gly Asp Pro Phe Ala Lys Leu Ile Val Glu Thr Asp
65                  70                  75                  80

Thr Phe Gly Ser Arg Val Arg Val Arg Gly Ala Glu Thr Gly Leu Tyr
                85                  90                  95

Ile Cys Met Asn Lys Lys Gly Lys Leu Ile Ala Lys Ser Asn Gly Lys
            100                 105                 110

Gly Lys Asp Cys Val Phe Thr Glu Ile Val Leu Glu Asn Asn Tyr Thr
            115                 120                 125

Ala Leu Gln Asn Ala Lys Tyr Glu Gly Trp Tyr Met Ala Phe Thr Arg
        130                 135                 140

Lys Gly Arg Pro Arg Lys Gly Ser Lys Thr Arg Gln His Gln Arg Glu
145                 150                 155                 160

Val His Phe Met Lys Arg Leu Pro Arg Gly His His Thr Thr Glu Gln
                165                 170                 175

Ser Leu Arg Phe Glu Phe Leu Asn Tyr Pro Pro Phe Thr Arg Ser Leu
                180                 185                 190

Arg Gly Ser Gln Arg Thr Trp Ala Pro Glu Pro Arg
            195                 200

<210> SEQ ID NO 4
<211> LENGTH: 753
<212> TYPE: DNA
<213> ORGANISM: Mus musculus

<400> SEQUENCE: 4
cgcaccttcg gcttgtcccc ccgcggcctc cagtgggacg gcgtgacccc gctcgggctc      60
tcagtgctcc ggggccgcg cgccatgggc agccccgct ccgcgctgag ctgcctgctg       120
ttgcacttgc tggttctctg cctccaagcc cagcatgtga gggagcagag cctggtgacg     180
```

```
gatcagctca gccgccgcct catccggacc taccagctct acagccgcac cagcgggaag    240
cacgtgcagg tcctggccaa caagcgcatc aacgccatgg cagaagacgg agacccttc    300 gcgaagctca ttgtggagac cgatactttt ggaagcagag tccgagttcg cggcgcagag    360
acaggtctct acatctgcat gaacaagaag gggaagctaa ttgccaagag caacggcaaa    420
ggcaaggact gcgtattcac agagatcgtg ctggagaaca actacacggc gctgcagaac    480
gccaagtacg agggctggta catggccttt acccgcaagg gccggccccg caagggctcc    540
aagacgcgcc agcatcagcg cgaggtgcac ttcatgaagc gcctgccgcg ggccaccac    600 accaccgagc agagcctgcg cttcgagttc ctcaactacc cgcccttcac gcgcagcctg    660
cgcggcagcc agaggacttg ggccccggag ccccgatagg cgctcgccca gctcctcccc    720
acccagccgg ccgaggaatc cagcgggagc tcg                                  753

<210> SEQ ID NO 5
<211> LENGTH: 615
<212> TYPE: DNA
<213> ORGANISM: Rattus norvegicus

<400> SEQUENCE: 5
atgggcagcc cccgctccgc gctgagctgc ctgctgttgc acttgctggt tctctgcctc    60
caagcccagc atgtgaggga gcagagcctg gtgacggatc agctcagccg ccgcctcatc    120
cggacctacc agctctacag ccgcaccagc gggaagcacg tgcaggtcct ggccaacaag    180
cgcatcaacg ccatggcaga agacggagac cccttcgcaa agctcattgt ggagaccgat    240
acttttggaa gcagagtccg agtccgcgga gcagagaccg gtctgtacat ctgcatgaac    300
aagaagggga gctaatcgc aagagcaac ggcaaaggca aggactgcgt gttcacggag    360
atcgtgctgg agaacaacta cacggcgctg cagaacgcca agtacgaggg ctggtacatg    420
gcctttaccc gcaagggccg gccccgcaag ggttccaaga cgcgccagca ccagcgcgag    480
gtgcacttca tgaagcgcct gccgcggggc caccacacca cagagcagag cctccgcttc    540
gagttcctca actacccgcc cttcacgcgc agcctgcgcg gcagccagag gacttgggcc    600
ccggagcccc gatag                                                      615

<210> SEQ ID NO 6
<211> LENGTH: 615
<212> TYPE: DNA
<213> ORGANISM: Homo sapiens

<400> SEQUENCE: 6
atgggcagcc cccgctccgc gctgagctgc ctgctgttgc acttgctggt cctctgcctc    60
caagcccagc atgtgaggga gcagagcctg gtgacggatc agctcagccg ccgcctcatc    120
cggacctacc aactctacag ccgcaccagc gggaagcacg tgcaggtcct ggccaacaag    180
cgcatcaacg ccatggcaga ggacggcgac cccttcgcaa agctcatcgt ggagacggac    240
acctttggaa gcagagtccg agtccgcgga gccgagacgg cctctacat ctgcatgaac    300 aagaagggga gctgatcgc aagagcaac ggcaaaggca aggactgcgt cttcacggag    360
attgtgctgg agaacaacta cacagcgctg cagaatgcca agtacgaggg ctggtacatg    420
gccttcaccc gcaagggccg gccccgcaag ggctccaaga cgcggcagca ccagcgtgag    480
gtccacttca tgaagcggct gccccggggc caccacacca ccgagcagag cctgcgcttc    540
```

-continued

```
gagttcctca actacccgcc cttcacgcgc agcctgcgcg gcagccagag gacttgggcc        600
ccggagcccc gatag                                                         615
```